US007426030B1

(12) United States Patent
Liphardt et al.

(10) Patent No.: US 7,426,030 B1
(45) Date of Patent: Sep. 16, 2008

(54) REDUCED GAS FLOW PURGING SYSTEM IN REFLECTOMETER, ELLIPSOMETER, POLARIMETER AND THE LIKE SYSTEMS

(75) Inventors: Martin M. Liphardt, Lincoln, NE (US); James D. Welch, Omaha, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 106 days.

(21) Appl. No.: 11/704,545

(22) Filed: Feb. 10, 2007

Related U.S. Application Data

(60) Continuation-in-part of application No. 11/145,470, filed on Jun. 6, 2005, now Pat. No. 7,327,456, and a continuation-in-part of application No. 11/105,852, filed on Apr. 14, 2005, and a continuation-in-part of application No. 10/925,333, filed on Aug. 24, 2004, and a continuation-in-part of application No. 10/925,333, filed on Aug. 24, 2004, and a continuation-in-part of application No. 10/849,740, filed on May 20, 2004, and a continuation-in-part of application No. 10/829,620, filed on Apr. 22, 2004, and a continuation-in-part of application No. 10/829,620, filed on Apr. 22, 2004, and a continuation-in-part of application No. 10/376,677, filed on Feb. 28, 2003, now Pat. No. 6,982,792, and a continuation-in-part of application No. 10/178,723, filed on Jun. 24, 2002, now Pat. No. 6,950,182, and a continuation-in-part of application No. 10/050,802, filed on Jan. 15, 2002, now Pat. No. 6,859,278, and a division of application No. 10/050,802, filed on Jan. 15, 2002, and a continuation-in-part of application No. 09/864,840, filed on May 24, 2001, now Pat. No. 6,456,376, and a continuation-in-part of application No. 09/854,548, filed on May 14, 2001, now abandoned, and a continuation-in-part of application No. 09/583,229, filed on May 30, 2000, now Pat. No. 6,804,004, and a continuation-in-part of application No. 09/531,877, filed on Mar. 21, 2000, now Pat. No. 6,535,286.

(60) Provisional application No. 60/772,926, filed on Feb. 13, 2006, provisional application No. 60/300,714, filed on Jun. 26, 2001, provisional application No. 60/424,589, filed on Nov. 7, 2002, provisional application No. 60/427,043, filed on Nov. 18, 2002, provisional application No. 60/431,489, filed on Dec. 6, 2002, provisional application No. 60/564,747, filed on Apr. 23, 2004, provisional application No. 60/580,314, filed on Jun. 17, 2004, provisional application No. 60/261,243, filed on Jan. 16, 2001, provisional application No. 60/263,874, filed on Jan. 25, 2001, provisional application No. 60/287,784, filed on May 2, 2001.

(51) Int. Cl.
*G01J 4/00* (2006.01)
(52) U.S. Cl. .................... 356/369; 356/367
(58) Field of Classification Search ................ 356/369, 356/364, 367, 445
See application file for complete search history.

(56) References Cited

U.S. PATENT DOCUMENTS

| 4,824,248 | A | * | 4/1989 | Neumann ................ 356/244 |
|---|---|---|---|---|
| 5,582,646 | A | | 12/1996 | Woollam et al. ........... 118/708 |
| 6,628,397 | B1 | * | 9/2003 | Nikoonahad et al. ....... 356/445 |
| 6,813,026 | B2 | | 11/2004 | McAninch ................ 356/445 |

* cited by examiner

*Primary Examiner*—Roy M Punnoose
(74) *Attorney, Agent, or Firm*—James D. Welch

(57) ABSTRACT

Reflectometer, ellipsometer, polarimeter or the like system, which functionally comprise means for providing gas confined in a mini-chamber near the surface of a sample, at a location at which a beam having UV, VUV, IR and NIR wavelengths of electromagnetic radiation is caused to be impinged thereupon.

5 Claims, 9 Drawing Sheets

PREVIOUS DISCLOSED ART

REDUCED GAS FLOW PURGING SYSTEM IN REFLECTOMETER, ELLIPSOMETER, POLARIMETER AND THE LIKE SYSTEMS

This application Claims Benefit of Provisional Application Ser. No. 60/772,926 Filed Feb. 13, 2006; and is a CIP of application Ser. No. 11/145,470 Filed Jun. 6, 2005 now U.S. Pat. No. 7,327,456, and there via of Ser. No. 10/376,677 Filed Feb. 28, 2003 now U.S. Pat. No. 6,982,792 and from Ser. No. 09/531,877 Filed Mar. 21, 2000 now U.S. Pat. No. 6,535,286; and from 10/178,723 filed Jun. 24, 2002 now U.S. pat. No. 6,950,182; and 09/583,229 filed May 30, 2000 now U.S. Pat. No. 6,804,004; and from 09/864,840 filed May 24, 2001 now U.S. Pat. No. 6,456,376; and 09/854,548 filed May 14, 2001 now abandoned; and Claims benefit of Provisional Application Ser. Nos. 60/300,714 filed Jun. 26, 2001, and 60/424,589 filed Nov. 7, 2002, and 60/427,043 filed Nov. 18, 2002 and 60/431,489 filed Dec. 6, 2002. This Application also is a CIP of Co-Pending application Ser. No. 10/849,740 Filed May 20, 2004. This application is also a CIP of Pending application Ser. No. 11/105,852 Filed Apr. 14, 2005 also there via Claims benefit of Provisional Applications 60/564,747 Filed Apr. 23, 2004, and 60/580,314 Filed Jun. 17, 2004. This application is further a Continuation-In-Part of Utility application Ser. Nos. 10/829,620 Filed Apr. 22, 2004; and of 10/925,333 Filed Aug. 24, 2004, and there via of 10/050,802 Filed Jan. 15, 2002, (now U.S. Pat. No. 6,859,278). This application is further a Continuation-In-Part of Utility application Ser. No. 10/925,333 Filed Aug. 24, 2004, and of 10/829,620 Filed Apr. 22, 2004, and is a Divisional of 10/050,802 Filed Jan. 15, 2002; and via the above Applications claims Benefit of Provisional Application Ser. No. 60/261,243 Filed Jan. 16, 2001, 60/263,874 Filed Jan. 25, 2001, 60/287,784 Filed May 2, 2001.

TECHNICAL FIELD

The disclosed invention relates to reflectometer, ellipsometer, polarimeter and the like systems, and more particularly to a reflectometer, ellipsometer, polarimeter or the like system, which functionally comprises means for providing gas confined in a "mini-chamber" near the surface of a sample, at a location at which a beam of electromagnetic radiation is caused to be impinged thereupon.

BACKGROUND

To begin, it is noted that Spectroscopic Ellipsometry (SE) was developed in the early 1970's after single wavelength ellipsometry had gained widespread acceptance. The first (SE) systems provided limited Ultraviolet (UV) to near Infrared (IR) spectral range capability, and with the exception of a few research instruments, this remained the case until the 1990's. Many challenges faced development of (VUV) ellipsometer systems, including the fact that many optical element materials absorb in the (VUV) wavelength range. Vacuum Ultraviolet (VUV) ellipsometry was so named as it was initially carried out in vacuum, however, the terminology is today applied where purging gas such as nitrogen is utilized in place of vacuum at wavelengths, typically with an energy less than about 10 ev. The reason (VUV) ellipsometry must be carried out in vacuum or purging gas is that (VUV) wavelengths, are absorbed by oxygen and water vapor.

In the mid-1980's a Spectroscopic ellipsometer was constructed at the BESSY Synchrotron in Berlin for application in the (VUV) wavelength range, (eg. 5-35 eV), and in the 1990's Spectroscopic ellipsometry was achieved in the Extreme Ultraviolet (EUV) range, (eg. greater than 35 eV), at KEK-PF. Application of ellipsometry in the (VUV) and (EUV) wavelength ranges remained restricted to said research facilities until in 1999 commercial (VUV) ellipsometer systems became available from companies such as the J.A. Woollam Co. Inc. At present there are approximately twenty-five (VUV) Systems in use worldwide. It is noted that commercial (VUV) instruments, which provided wavelengths down to 146 nm, were introduced in response to the need for bulk material properties at 156 nm, which is utilized in lithography as applied to semiconductor gate oxide production. It is disclosed that a known patent which provides for use of VUV wavelength electromagnetic radiation through 10 eV is No. 6,414,302 B1 to Freeouf.

Continuing, the practice of ellipsometry, polarimetry, spectrophotometry, reflectometry, scatterometry and the like, using Infrared (IR), (eg. 2-33 micron), and Ultraviolet. (UV), (eg. 135-1700 nm), Electromagnetic Radiation Wavelengths, then is, as disclosed above, known. As mentioned, electromagnetic Radiation with wavelengths below about 190 nm is absorbed by atmospheric components such as Oxygen and Water Vapor. Thus, practice of Ellipsometry etc. using UV Wavelengths is typically carried out in vacuum or an atmosphere which does not contain oxygen and/or water vapor or other absorbing components. The J.A. Woollam CO. VUV-VASE, (Registered Trademark), for instance, utilizes a substantially enclosed Chamber which encompasses a substantially enclosed space which during use is purged by Nitrogen and/or Argon or functionally equivalent gas. (Note Nitrogen does not significantly absorb UV Range wavelengths, and Argon is in some respects even a better choice). A problem with practicing Ellipsometry etc. however, where the sample is in a substantially enclosed, internal ambient controlled, chamber is that it is often inconvenient to access what is contained therewithin without entering oxygen or water vapor etc. thereinto. As a result, the J.A. Woollam Co. VUV-VASE, (Registered Trademark), System comprises a means for causing a subspace sequestering means to become configured so as to sequester a sample in a subspace of said substantially enclosed space during entry and removal of a sample. This allows accessing a sample means for placing and maintaining a sample in a desired position and orientation, (ie. a sample supporting stage), with the benefit that only the sequestered subspace then needs substantial purging. The subspace sequestering means further enables reconfiguration to open the entire substantially enclosed space in the chamber to the sample, thereby facilitating its access thereof via UV range wavelength electromagnetic radiation.

It is noted that the J.A. Woollam Co. VUV-VASE includes two-speed purge control means, such that a sequestered subspace can be purged, quickly, but when purging is substantially complete, a Nitrogen conserving slower maintenance purge speed can be effected. This is important as it provides a means of expense reduction via gas conservation.

A U.S. Pat. No. 6,813,026 to McAninch is disclosed as it describes a purge system for application in optical metrology tools. This patent describes a system which, rather than purge a chamber in which a sample is present, includes means for flowing a gas over the surface of a sample at a location thereon at which an electromagnetic beam is caused to impinge. Present are an optics plate for supporting measurement optics and a movable stage. The lower surface of the optics plate is claimed as being planar in the 026 patent. During use inert gas is injected between the lower planar surface of the optics plate and the upper surface of a sample. The gas flow also serves to clear the measurement area of the sample of absorbing species. It is noted that the gas flow is continuous during use and that no provision for conserving gas is provided.

For additional insight it is noted that while present invention systems can be applied in any material system investigation system such as Polarimeter, Reflectometer and the like Systems, an important application is in Ellipsometer Systems, whether monochromatic or spectroscopic, which operate in a ultraviolet (UV), vacuum ultraviolet (VUV), infrared (I.R) or near infrared (NIR) wavelength range. It should therefore be understood that Ellipsometry involves acquisition of sample characterizing data at single or multiple Wavelengths, and at one or more Angle(s)-of-Incidence (AOI) of a Beam of Electromagnetic Radiation to a surface of the sample. Ellipsometry is generally well described in a great many number of publications, one such publication being a review paper by Collins, titled "Automatic Rotating Element Ellipsometers: Calibration, Operation and Real-Time Applications", Rev. Sci. Instrum, 61(8) (1990).

It is also noted that a typical goal in ellipsometry is to obtain, for each wavelength in, and angle of incidence of said beam of electromagnetic radiation caused to interact with a sample, characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$, caused by interaction with said sample:

$$\frac{r_p}{r_s} = \rho = \tan\Psi \cdot \exp(i \cdot \Delta).$$

Continuing, Ellipsometer systems generally include a source of a beam of electromagnetic radiation, a Polarizer, which serves to impose a known, (typically linear), state of polarization on a beam of electromagnetic radiation, a Stage for supporting a sample, and an Analyzer which serves to select a polarization state in a beam of electromagnetic radiation after it has interacted with a material system, and pass it to a Detector System for analysis therein. As well, one or more Compensator(s) can be present and serve to affect a phase retardance between orthogonal components of a polarized beam of electromagnetic radiation. A number of types of ellipsometer systems exist, such as those which include rotating elements and those which include modulation elements. Those including rotating elements include Rotating Polarizer (RP), Rotating Analyzer (RA) and Rotating Compensator (RC). A preferred embodiment is a Rotating Compensator Ellipsometer System because they do not demonstrate "Dead-Spots" where obtaining ellipsometric data is difficult. They can read PSI and DELTA of a Material System over a full Range of Degrees with the only limitation being that if PSI becomes essentially zero (0.0), one can't then determine DELTA as there is not sufficient PSI Polar Vector Length to form the angle between the PSI Vector and an "X" axis. In comparison, Rotating Analyzer and Rotating Polarizer Ellipsometers have "Dead Spots" at DELTA's near 0.0 or 180 Degrees and Modulation Element Ellipsometers also have a "Dead Spot" at PSI near 45 Degrees). The utility of Rotating Compensator Ellipsometer Systems should then be apparent. Another benefit provided by Rotating Compensator Ellipsometer Systems is that the Polarizer (P) and Analyzer (A) positions are fixed, and that provides benefit in that polarization state sensitivity to input and output optics during data acquisition is essentially non-existent. This enables relatively easy use of optic fibers, mirrors, lenses etc. for input/output.

Typical construction of spectrophotometer, reflectometer, polarimeter, ellipsometer and the like systems, (eg. Rotating Analyzer, Rotating Polarizer, Rotating Compensator, Modulator Element Ellipsometer) provides a Sample Supporting Stage which is substantially fixed in location. Functionally oriented with respect thereto are a Substantially Fixed Position Source Means (S) for providing a beam of electromagnetic radiation at an oblique angle to said Sample Supporting Stage, and a Substantially Fixed Position Data Detector Means (D) for intercepting Electromagnetic Radiation which Reflects (or Transmits through), a Sample placed on said Sample Supporting Stage. Typical procedure is to place a Sample onto the Sample Supporting Stage, cause a beam of Electromagnetic Radiation to impinge thereonto, and record data produced by the Data Detector Means in response to electromagnetic radiation which enters thereinto, which data is analyzed to provide insight into Sample Optical and Physical properties. Said procedure can include adjustment of the Sample Supporting Stage, or the source and detector of electromagnetic radiation in an "X"-"Y" Plane, and along a "Z" direction perpendicular to its surface, (ie. a vertical position adjustment where the Electromagnetic Radiation approaches the Sample at an oblique angle from a laterally located Source). This purpose of said "Z" adjustment is, for instance, to enable the directing of a beam of Electromagnetic Radiation Reflected from a Sample placed on said Sample Supporting Stage into the Data Detector without moving the Data Detector so it intercepts a beam exiting said Sample. It should be appreciated then that conventional Reflectometer, Ellipsometer and Polarimeter Systems which include provision for such Sample positioning adjustment and orientation with respect to an impinging Electromagnetic beam, typically do so by allowing the Sample Supporting Stage position to be adjusted, rather than by effecting simultaneous change in location of the Source and Data Detector with respect to the Sample Supporting Stage, because it is far simpler to implement Sample Supporting Stage location change. However, an alternative is mount a Reflectometer, Spectrophotometer, Ellipsometer, Polarimeter or the like System to a means for moving it in an "X"-"Y" Plane, and along a "Z" direction perpendicular to its surface of the Sample with respect to a substantially fixed position Stage for supporting a Sample. In either case, however, a relative motion occurs between the Reflectometer, Ellipsometer, Polarimeter or the like System and a sample.

Even in view of the prior art, need remains for improvements to systems and methodology for investigating samples with electromagnetic radiation at wavelengths which are absorbed by, for instance, oxygen and water vapor present in the atmosphere.

DISCLOSURE OF THE INVENTION

As disclosed, in the Background Section, Ultraviolet (UV), vacuum Ultraviolet (VUV) Infra-Red (IR) or Near Infrared (NIR) Wavelengths are absorbed by oxygen or water vapor, hence where they are applied to a sample by a Reflectometer, Ellipsometer, Polarimeter or the like system, it is necessary to evacuate and/or purge at least the region around a sample, and preferably along the pathway of the electromagnetic radiation from the source thereof, to a detector thereof.

With the foregoing in mind, it is disclosed that the present invention comprises a:

reflectometer;
ellipsometer;
spectroscopic ellipsometer;
polarimeter; or
spectroscopic polarimeter;

system for investigating a sample with electromagnetic radiation comprising:

a source of electromagnetic radiation and a detector of electromagnetic radiation oriented such that in use said source of electromagnetic radiation provides a beam of electromagnetic radiation at an angle of incidence to a surface of a sample, and said detector of electromagnetic radiation receives a resulting beam of electromagnetic radiation reflected therefrom.

Said source and detector of electromagnetic radiation are functionally mounted to a common placement means, and said sample is present on a separate stage. The system further comprises means for causing relative motion between said source and detector of electromagnetic radiation as a unit, and said sample. Said system further comprises interface means for providing slidable contact or substantial slidable contact between said common placement means and said separate stage such that a mini-chamber which accesses said sample is formed thereby. Said system further comprising means for introducing gas into said mini-chamber and means for displaying data provided by the detector of electromagnetic radiation.

The present invention system can comprise an ellipsometer or polarimeter system for analyzing sample systems using electromagnetic radiation with wavelengths in the ultraviolet, vacuum ultraviolet, infrared or near infrared wavelength range, said ellipsometer system comprising a mini-chamber which accesses at least a portion of a sample; said ellipsometer or polarimeter system further comprising:

a) source means for providing of a beam including ultraviolet, vacuum ultraviolet, infrared or near infrared wavelength range electromagnetic radiation;

b) polarization state setting means for setting a polarization state in at least a selected range of wavelengths in a beam including ultraviolet, vacuum ultraviolet, infrared or near infrared wavelength range electromagnetic radiation;

c) a means for placing and maintaining a sample system in a desired position and orientation, said means for placing and maintaining a sample system in a desired position and orientation such that at least a portion of a sample can be sequestered by said mini-chamber;

d) data detector means for receiving an electromagnetic beam which is caused to interact with a sample which is secured in place by said means for placing and maintaining a sample system in a desired position and orientation;

e) computer means for analyzing at least some data provided by said data detector means for receiving an electromagnetic beam after it interacts with said sample and/or storing at least some of said data and/or an analyzed version thereof in machine readable media and/or displaying at least some of said data and/or an analyzed version thereof electronically or by non-electronic means, and/or causing at least some of said data and/or an analyzed version thereof to be represented by a signal which is applied to provide a concrete and tangible result.

Said source means and polarization state setting means and data detector means are all functionally associated with a common placement means which can be positioned to slidably contact or substantially slidably contact said means for placing and maintaining a sample system in a desired position and orientation via interface means, such that when actual or substantial slidable contact is effected a mini-chamber is formed between said common placement means and said means for placing and maintaining a sample system in a desired position and orientation, said mini-chamber accesses at least a part of said sample. Said common placement means can be of single or multiple piece construction. Said mini-chamber further has means functionally affixed thereto for effecting evacuation and/or entering purging gas into said mini-chamber. In use a sample is caused to be positioned and oriented by said means for placing and maintaining a sample in a desired position and orientation, and actual or substantial slidable contact is realized between said common placement means and said means for placing and maintaining a sample in a desired position and orientation, via said interface means. Purging gas is then caused to be entered into said mini-chamber, and said source means for providing of a beam including ultraviolet, vacuum ultraviolet, infrared or near infrared wavelength range electromagnetic radiation is caused to provide a beam including ultraviolet vacuum ultraviolet, infrared and/or near infrared wave lengths. Said polarization state setting means for setting a polarization state in a selected range of wavelengths in a beam including electromagnetic radiation is caused to impose a polarization state thereupon and said resulting beam of electromagnetic radiation is caused to reflect from said sample and enter said data detector. Said computer means is then applied to analyze data provided by said data detector and display it and/or an analyzed version thereof, and/or store at least some of said data and/or an analyzed version thereof in machine readable media, and/or causing at least some of said data and/or an analyzed version thereof to be represented by a signal which is applied to provide a concrete and tangible result.

It is noted that an ellipsometer or polarimeter can be considered to comprise a Polarization State Generator, (which comprises a source of electromagnetic radiation and a means for imposing a polarization state thereupon, a Stage for supporting a Sample, and a Polarization State Detector which comprises a polarization state analyzer and a data detector. The present invention system can then be recited as an ellipsometer or polarimeter comprising sequentially, a polarization state generator, a stage for supporting a sample and a polarization state detector, wherein said polarization state generator and polarization state detector are functionally associated with a common placement means which can be positioned to slidably contact or substantially contact said stage via interface means. When said slidable contact is effected a mini-chamber is formed between said common placement means and said stage with said mini-chamber accessing at least a part of a surface of said sample. Said mini-chamber further has means functionally affixed thereto for effecting evacuation and/or entering purging gas into said mini-chamber such that in use a sample is caused to be positioned on said stage and actual or substantial slidable contact realized between said common placement means and said stage via said interface means. Then purging gas is caused to be entered into said mini-chamber, and said polarization state generator is caused to provide a beam electromagnetic radiation which is directed to reflect from said sample and enter said data detector; said computer means is applied to analyze data provided by said data detector, and said data per se. or results of analysis thereof can be displayed and/or stored and or used to form a signal representing it.

The improvement provided by the present invention is a means for providing gas sequestered in a formed "mini-chamber" in the vicinity of a location on a surface of a sample during investigation thereof by electromagnetic radiation. While similar in purpose to the system described in U.S. Pat. No. 6,813,026 to McAninch, taking guide from the J.A. Woollam VUV system described briefly in the Background Section, which provides a reduced gas flow mode, the present invention does not require a continuous flow of gas during use. Rather, the present invention system provides means for forming a "mini-chamber" which accesses therewithin at least a portion of a sample. The method of use of the present invention can involve a period of flowing gas over a sample surface to, for instance, remove debris, but then there is formed a gas conserving "mini-chamber" which accesses at least a portion of said sample. Investigation of said sample with electromagnetic radiation comprising wavelengths in, for instance, the IR and/or UV and VUV ranges, which wavelengths are absorbed by ambient atmospheric component such as oxygen and water vapor, is then performed. It is noted that data pertaining to wavelengths not absorbed by Oxygen and/or Water Vapor can be obtained during an evacuation and/or purging procedure before said procedure is completed. This structured data collection approach allows an efficient use of time.

A method enabled by the present invention involves analyzing sample with spectroscopic electromagnetic radiation comprised of wavelengths which are absorbed by oxygen and/or water vapor comprises the steps of:

in any functional order practicing steps a, a' and a":
- a) providing a system for forming a mini-chamber which encloses a substantially enclosed space which accesses at least a portion of a sample, to which mini-chamber is functionally affixed a means for evacuating or purging said substantially enclosed space of oxygen and/or water vapor, and means for entering a beam of electromagnetic radiation thereinto, and a means for exiting electromagnetic radiation therefrom; and
- a') providing a source of a spectroscopic beam electromagnetic radiation comprised of wavelengths which are absorbed by oxygen and/or water vapor and wavelengths which are not absorbed by oxygen and/or water vapor; and
- a") providing a data detector of spectroscopic electromagnetic radiation and means for displaying detected data.

Said method then proceeds with practice of steps b and c:
- b) positioning a sample in said system for forming a mini-chamber which encloses a substantially enclosed space which accesses at least a portion of a sample;
- c) causing said means for evacuating or purging said substantially enclosed space of oxygen and/or water vapor to tangibly and concretely evacuate or purge said substantially enclosed space of oxygen and/or water vapor, and causing said source of a spectroscopic beam electromagnetic radiation comprised of wavelengths which are absorbed by oxygen and/or water vapor to provide a beam of said electromagnetic radiation comprised of wavelengths which are absorbed by oxygen and/or water vapor to enter said means for entering a beam of electromagnetic radiation along a locus, such that it interacts with said sample, reflects therefrom, and exits said means for exiting electromagnetic radiation and enters said detector of spectroscopic electromagnetic radiation.

The result is that when said substantially enclosed space is sufficiently evacuated or purged of oxygen and/or water vapor, data is provided by said data detector for wavelengths which are absorbed by oxygen and/or water vapor.

A modified method of investigating a sample with spectroscopic electromagnetic radiation comprised of wavelengths which are absorbed by oxygen and/or water vapor and wavelengths which are not absorbed by oxygen and/or water vapor, comprises a modified procedure wherein during the evacuation or purging process, while oxygen and/or water vapor is still present in said substantially enclosed space in sufficient quantity to absorb said wavelengths which are absorbed by said oxygen and/or water vapor, data is provided by said data detector for wavelengths which are not absorbed by oxygen and/or water vapor, and such that once said substantially enclosed space is sufficiently evacuated or purged of oxygen and/or water vapor, data is provided by said data detector for wavelengths which are absorbed by oxygen and/or water vapor.

Both of the foregoing methods can then involve performing at least one selection from the group consisting of:
- storing at least some data provided by said data detector in machine readable media;
- analyzing at least some of the data provided by said data detector and storing at least some of the results of said analysis in machine readable media;
- displaying at least some data provided by said data detector by electronic and/or non-electronic means;
- analyzing at least some of the data provided by said data detector and displaying at least some of the results of said analysis by electronic and/or non-electronic means;
- causing at least some data provided by said data detector to produce a signal which is applied to provide a concrete and tangible result;
- analyzing at least some of the data provided by said data detector and causing at least some thereof to produce a signal which is applied to provide a concrete and tangible result.

The disclosed invention will be better understood by reference to the Detailed Description Section of this Specification, in coordination with the Drawings.

SUMMARY OF THE INVENTION

It is therefore a primary purpose and/or objective of the present invention to provide a reflectometer, ellipsometer, polarimeter or the like system, which functionally comprises means for providing evacuation and/or gas near the surface of a sample while a beam of electromagnetic radiation is caused to be impinged thereupon.

It is another purpose and/or objective of the present invention to provide evacuation and/or a flow of gas via a mini-chamber which accesses at least a portion of said sample at which a beam of electromagnetic radiation is caused to be impinged thereupon.

It is another purpose and/or objective of the present invention to describe a method of use of the present invention system to investigate a sample with wavelengths which are relatively less absorbed by ambient atmospheric components during period in which gas is flowed over a sample surface, and which then to investigate a sample with wavelengths which are substantially absorbed by ambient atmospheric components during period in which at least a portion of the sample which is being investigated is contained in a formed "mini-chamber" which contains gas.

Other purposes and/or objectives of the present invention will become apparent upon a reading of the Disclosure and Claims.

BRIEF DESCRIPTION OF THE DRAWINGS

FIG. 4d shows that a region (T) which is transparent to applicable wavelengths is present.

DETAILED DESCRIPTION

Figure 1A:
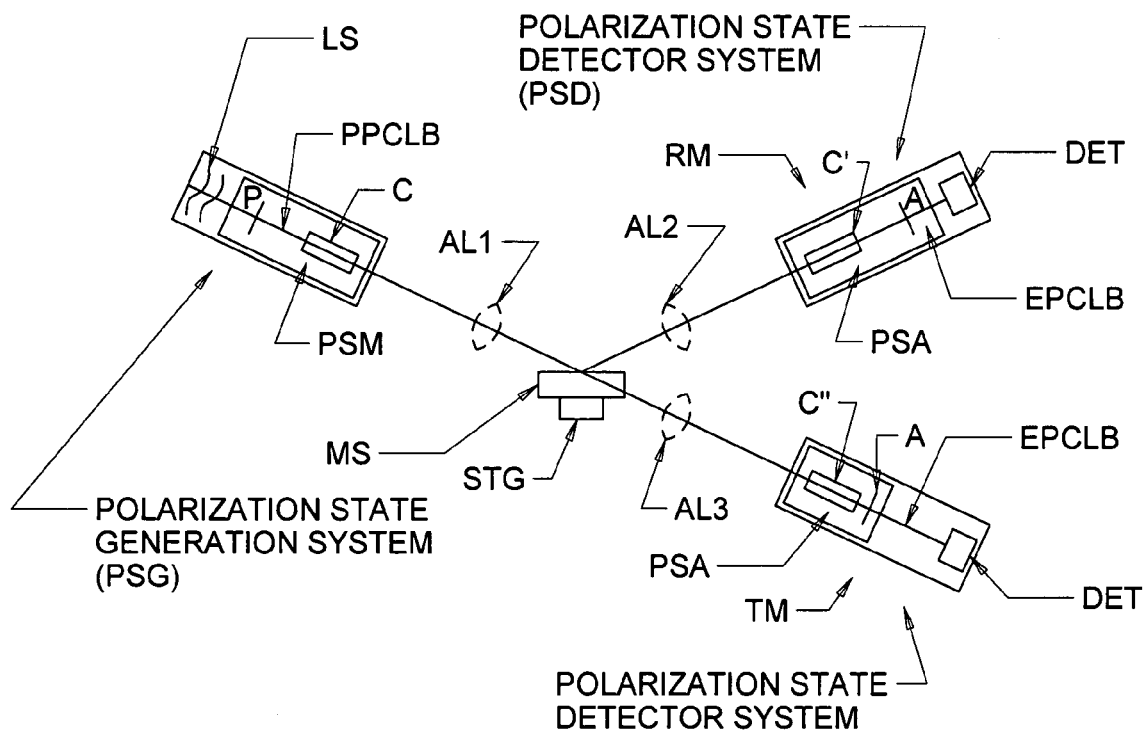
FIG. 1a shows a diagram of an ellipsometer system with both reflection and transmission detectors.

Turning to the Drawings, to provide insight to the state of the art, FIG. 1a shows a diagram of an ellipsometer/polarimeter system for use in both reflection (RF) and transmission (TM) modes. A source of monochromatic or polychromatic electromagnetic radiation (LS) is shown to, via polarization state modifier (PSM), which is demonstrated as being comprised of a Polarizer (P) and optionally a Compensator (C), provide a polarized beam of electromagnetic radiation (PPCLB) which is directed to interact with a material system (MS) which is placed on a stage (STG). (Note that conventional terminology identifies a Polarization State Generation System (PSG) as a combination of said source of monochromatic or polychromatic electromagnetic radiation (LS) and a Polarization State Modifier (PSM), which Polarization State Modifier (PSM) is demonstrated as being comprised of a Polarizer (P) and optionally a Compensator (C)). After interaction with the material system (MS), propagated electromagnetic beam (PPCLB) emerges as (EPCLB), after passing through a polarization state analyzer (PSA) and enters a detector system (DET). (Note that conventional terminology provides that for each of the Reflection (RM) and Transmission (TM) Modes, a Polarization State Analyzer (PSA) is demonstrated as being comprised of an Analyzer (A) and optionally a Compensator (C') or (C") respectively, and that when said Polarization State Analyzer (PSA) is combined with a Detector System (DET), there is formed a Reflection or Transmission Mode Polarization State Detector System (PSD), respectively). It is also to be understood that if the Polarization State Modifier (PSM), and Polarization State Analyzer (PSA) are not present, then FIG. 1a demonstrates a Spectrophotometer system comprised of (LS), (STG/(MS) and (DET). It is to be understood that the angle of incidence of the electromagnetic beam (PPCLB) is often oriented closer to normal to the material sample (MS) upper surface, when the system is operated as a Spectrophotometer. With regard to the present invention, it is to be appreciated that the Detector System(s) (DET) indicated can be multiple detector systems mounted on a positionable means (eg. a movable arm), thereby allowing easy alternate positioning of the Detector Systems in at least two locations. Note that such a rotation would be in a vertically oriented plane, but that this is only demonstrative and in any embodiment of the present invention multiple detector system, motion in any plane is within the scope of the Claims. In addition, it is noted that variously shaped apertures and/or focusing lenses (AL1) (AL2) (AL3), preferably achromatic, can be, but are not necessarily present before and/or after a sample as can functional equivalents to the polarizer/compensator/analyzer combinations.

Figure 1B:
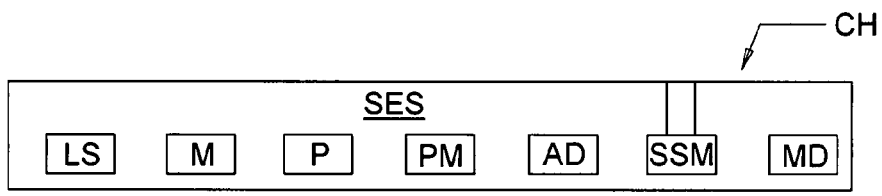
FIG. 1b shows a chamber (CH) which contains an essentially enclosed space (SES), with functional blocks corresponding to J.A. Woollam Co. VUV-VASE components therewithin.

There is shown in FIG. 1b a chamber (CH) which contains a substantially enclosed space (SES). Within said substantially enclosed space (SES) are shown functional blocks corresponding to Vacuum-Ultra-Violet Variable Angle Spectroscopic Ellipsometer (VUV-VASE) components. In particular, in said substantially enclosed space (SES) there is sequentially shown a source of polychromatic electromagnetic radiation (LS), a Monochromator (M), a polarization state setting means for setting a polarization state in at least a selected small range of wavelengths in a beam including ultraviolet wavelength range electromagnetic radiation (P); a means which enables sequentially modifying a polarization state set by said polarization state setting means, through a plurality of polarization states (PM); an alignment detector means (AD) which can comprise a plurality of detector elements surrounding a substantially centrally located hole through which a beam of electromagnetic radiation can pass, an indication of a subspace sequestering means (SSM) comprising means for placing and maintaining a sample in a desired position and orientation in a subspace sequestering means; and a multiple detector system (MD).

It should be appreciated that while the Monochromator (M) is shown in a specific position in FIG. 1b, but except for the source of electromagnetic radiation which must, of course be prior to the sample, can be moved to other locations in the system and be functional. Further, where Infrared wavelengths are desired, the source of polychromatic electromagnetic radiation (LS) and the Monochromator system can be replaced by an Infrared Fourier Transform (IR-FTIR) source system. And in addition, where a spectroscopic range of wavelengths of electromagnetic radiation are simultaneously utilized the monochromater can be deleted from FIG. 1b.

Figure 1C:
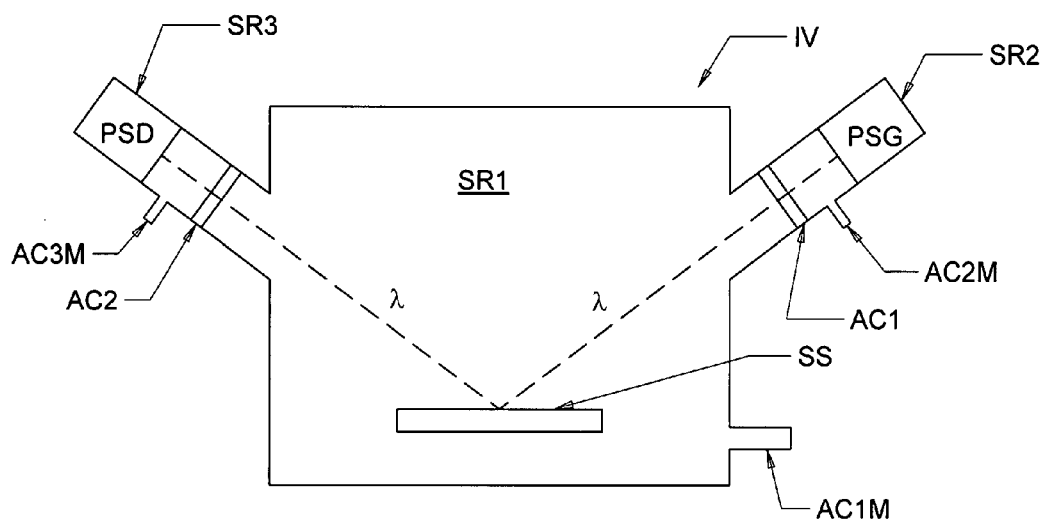
FIG. 1c demonstrates that an environmental control chamber can comprises multiple regions in which can be separately, or commonly sequestered Polarization State Generation System (PSG), Sample (SS) and Polarization State Generation Detector (PSD).

FIG. 1c demonstrates that an environmental control chamber can comprise multiple regions which can be separately sequestered. Shown are separate regions in which are present a Sample (SS), a Polarization State Generator (PSG) and a Polarization State Detector (PSD). Note that Ambient Control Means (AC1M), (AC2M) and (AC3M) are associated with said sequestered regions (SR1), (SR2) and (SR3) respectively and allow entry of purging gas or evacuation of their associated sequestered region. Sequestering Means (AC1) and (AC2), (eg. windows), separate the Sequestered Regions (SR2) from (SR1) and (SR1) from (SR3) respectively. The environment in each sequestered region can then be separately controlled.

Figure 1D:
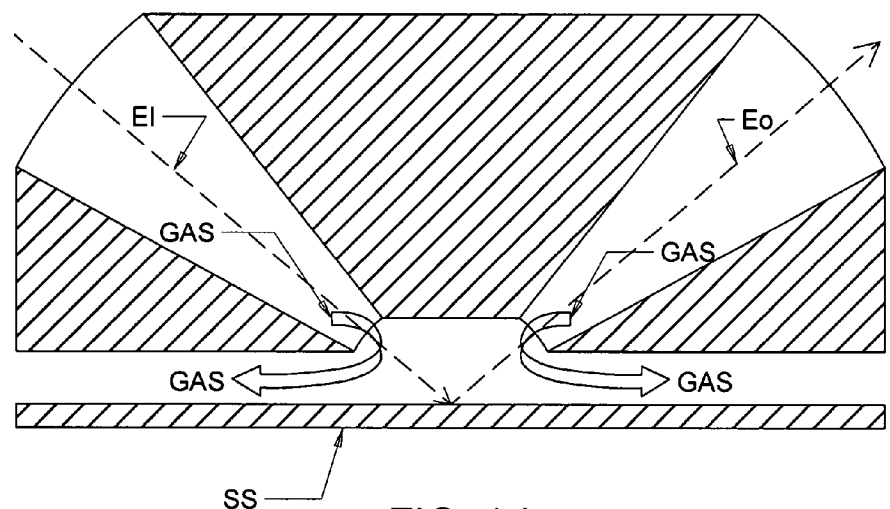
FIG. 1d demonstrates a system for flowing gas in the vicinity of a surface of a sample as described in U.S. Pat. No. 6,813,026 to McAninch.

FIG. 1d demonstrates a system for flowing gas in the vicinity of a surface of a sample as described in U.S. Pat. No. 6,813,026 to McAninch. Note that it is indicated as being entered through the "tubes" that allow electromagnetic radiation to enter and exit.

Figure 1E:
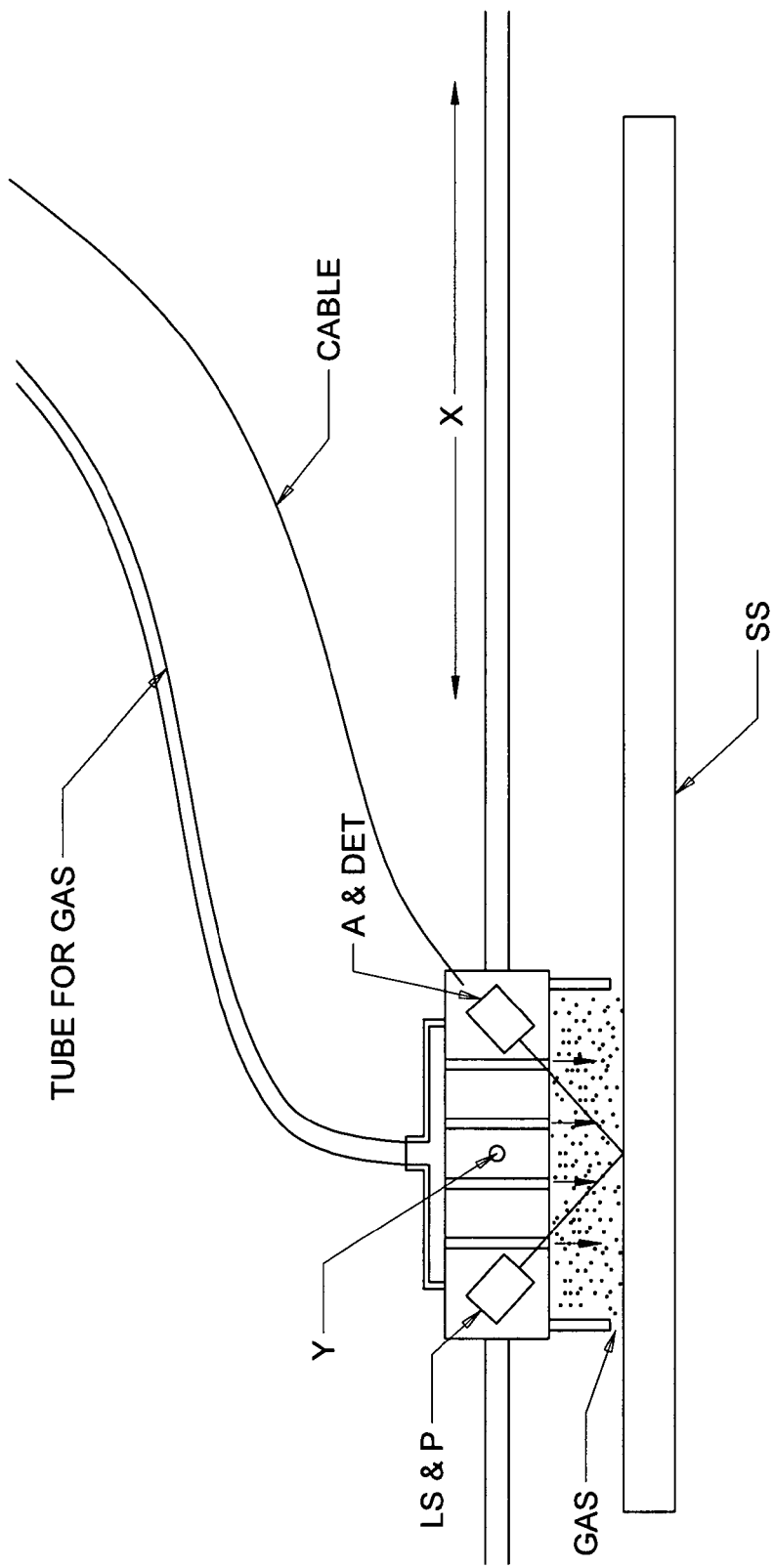
FIG. 1e shows a system for flowing gas near the surface of a sample as previously disclosed in Pending application Ser. No. 11/105,852 by Johs et al., which is Assigned to the J.A. Woollam CO. inc.

FIG. 1e shows a system for flowing gas near the surface of a sample as previously disclosed in Pending application Ser. No. 11/105,852 by Johs et al., which is Assigned to the J.A. Woollam CO. inc.

Figure 2:
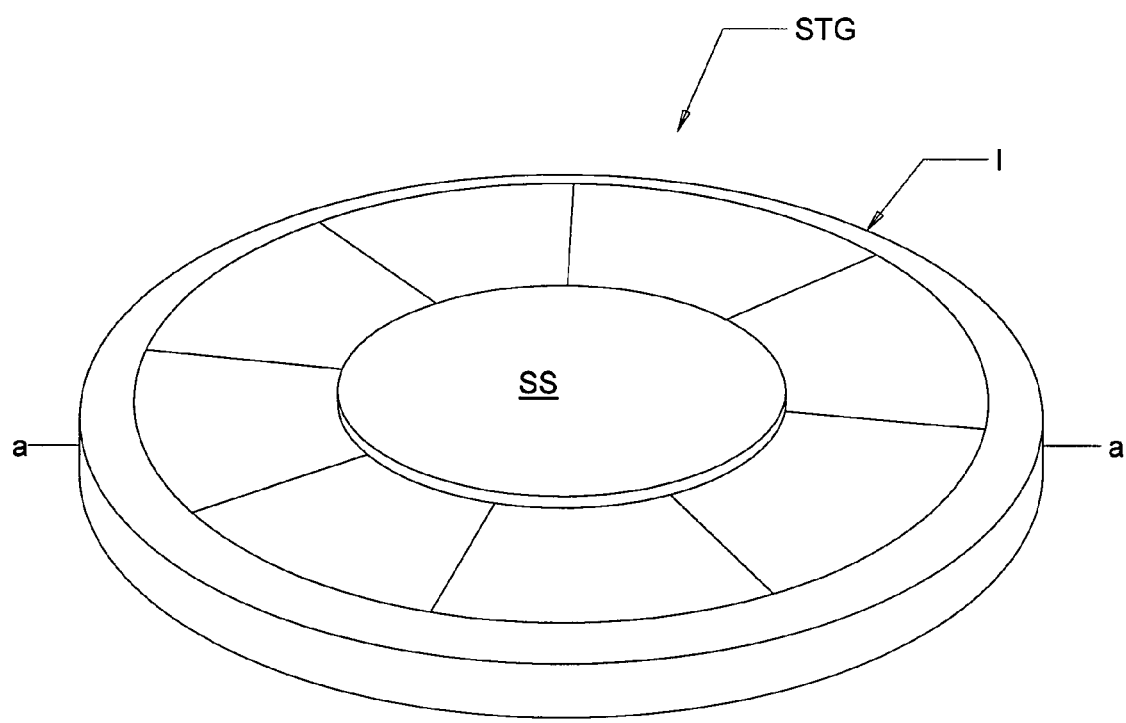
FIG. 2 shows a perspective view of a sample on a stage which includes an Interface (I) structure around its circumference.

FIG. 2 shows a perspective view of a Sample (SS) on a Stage (STG) which includes an Interface (I) structure around its circumference. Said Interface (I) can be a rigid or compliant structure and the surface thereof can be coated with a material such a teflon.

Figure 3A:
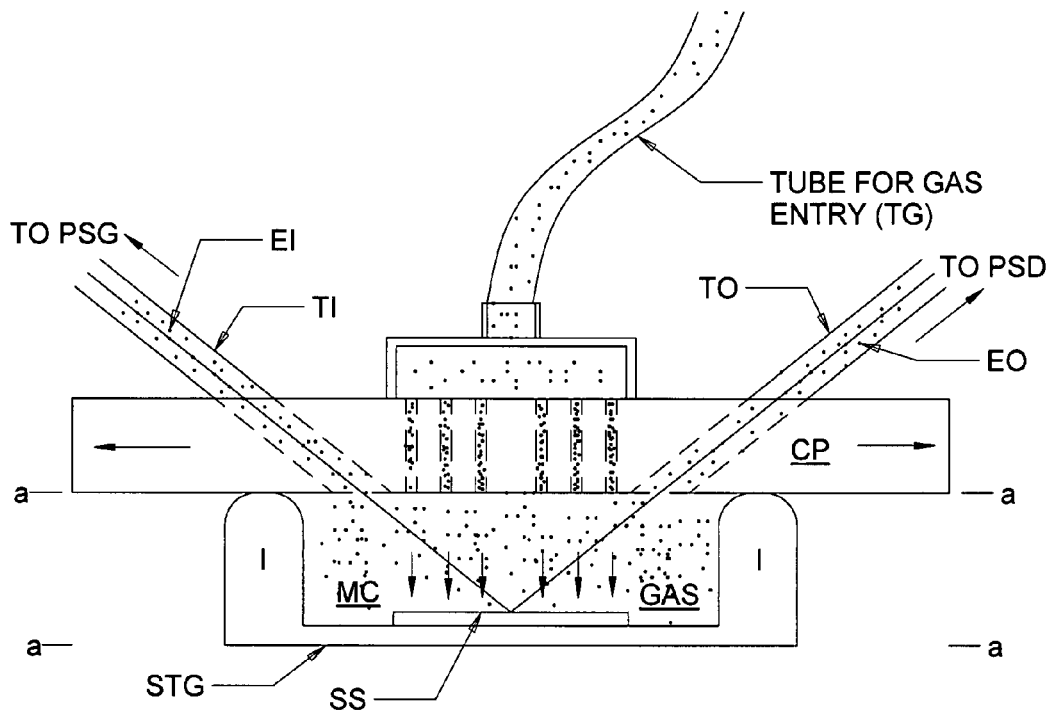
FIG. 3a shows a cross-sectional view taken a-a on FIG. 2, showing a Stage (STG) and Sample (SS), wherein the Interface Means (I) affixed to the Stage (STG) is in slidable contact with a Common Placement Means (CP) to which it is indicated is mounted a (PSG) and (PSD) of electromagnetic radiation.
Figure 3B:
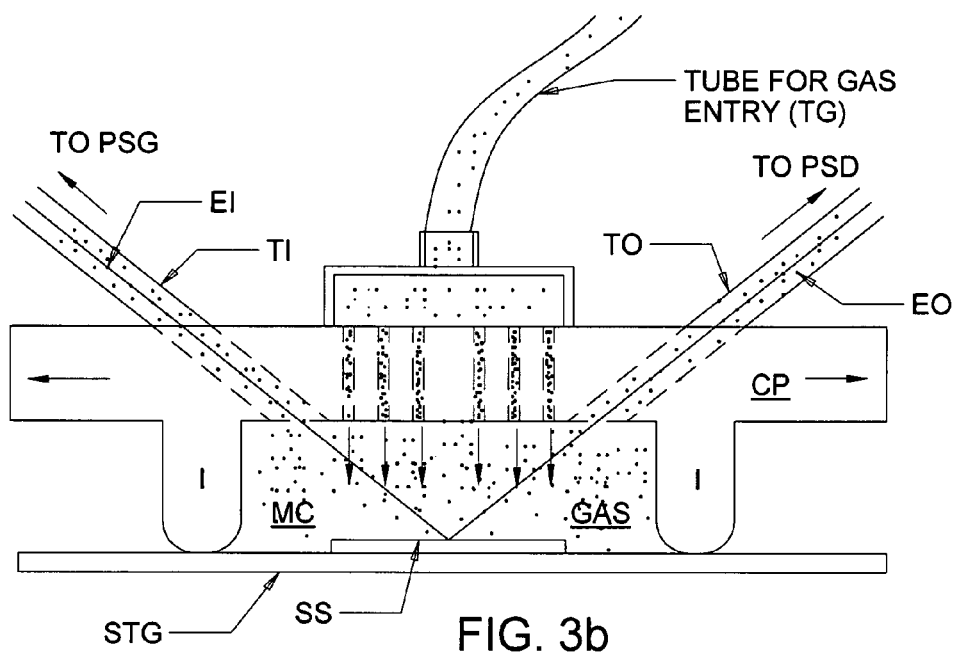
FIG. 3b shows a cross-sectional view as in FIG. 3a, but wherein the Interface Means (I) are affixed to the Common Placement Means (CP).
Figure 3C:
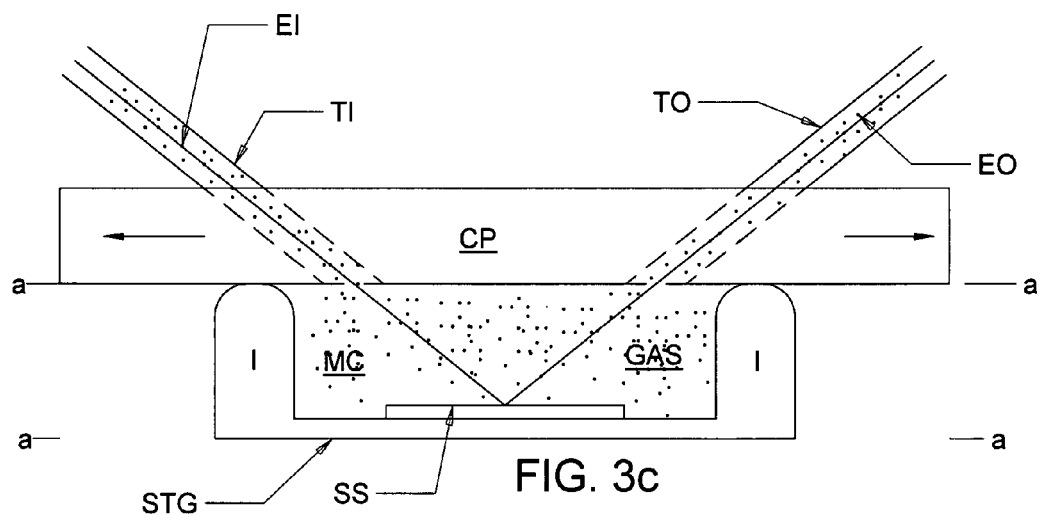
FIG. 3c shows a cross-sectional view taken a-a on FIG. 2, showing a Stage (STG) and Sample (SS), wherein the Interface Means (I) affixed to said Stage (STG) is in slidable contact with a Common Placement Means (CP) to which it is indicated is mounted a (PSG) and (PSD) of electromagnetic radiation.

FIG. 3a shows a cross-sectional view taken a-a on FIG. 2, showing a Stage (STG) and Sample (SS), wherein the Interface Means (I) affixed to the Stage (STG) is in slidable contact with a Common Placement Means (CP) to which it is indicated is mounted a (PSG) and (PSD) of electromagnetic radiation. Note that relative lateral motion of the Common Placement Means (CP) and Interface (I) is possible via sliding of the Common Placement Means (CP) over the Interface (I). FIG. 3b shows a cross-sectional view as in FIG. 3a, but wherein the Interface Means (I) are affixed to the Common Placement Means (CP) and a sliding lateral motion is enabled between the Interface Means (I) and the Stage STG). Note that FIGS. 3a and 3b provide separate GAS entry means via a Tube (TG) for Entering Gas. FIG. 3c shows a cross-sectional view taken a-a on FIG. 2, showing a Stage (STG) and Sample (SS), wherein the Interface Means (I) affixed to said Stage (STG) is in slidable contact with a Common Placement Means (CP) to which it is indicated is mounted a (PSG) and (PSD) of electromagnetic radiation. Note that the GAS is entered and exits through Tubes (TI) (TO) via which electromagnetic radiation (EI) (EO) is entered and exits. It is to be appreciated that the embodiments shown in FIGS. 3a and 3b can also provide GAS via the Tubes (TI) and (TO).

Figure 4C:
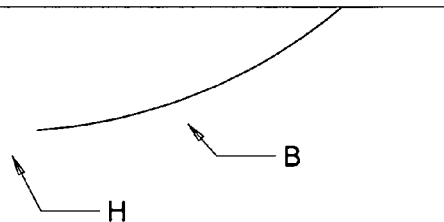
FIGS. 4c and 4d show two embodiments of a Bellows (B). Fig. a shows a small Hole (H) is present at a location whereat electromagnetic radiation would exit and impinge on a Sample (SS)
Figure 4D:
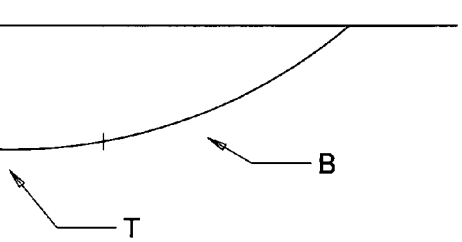
Figure 4A:
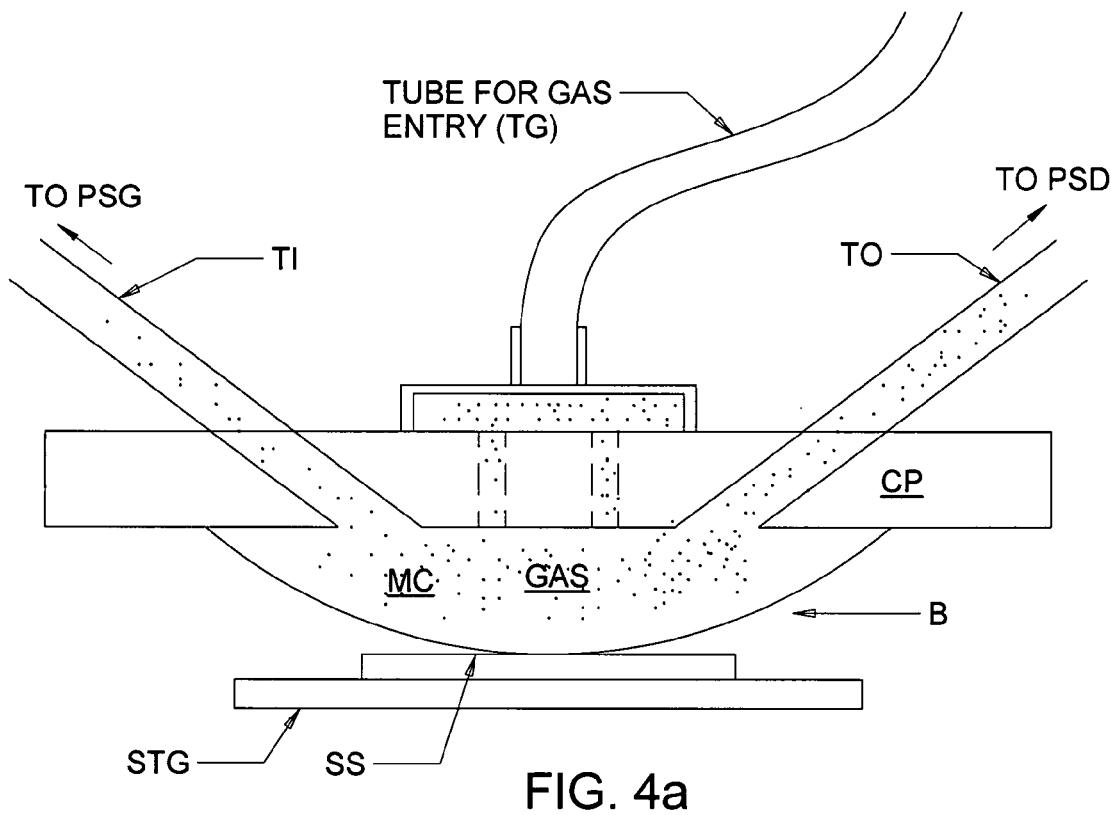
FIGS. 4a and 4b show a modified embodiment wherein a Bellows (B) is affixed to the Common Placement Means which in use is filled with gas such that it is placed directly adjacent to a surface of a Sample (SS).
Figure 4B:
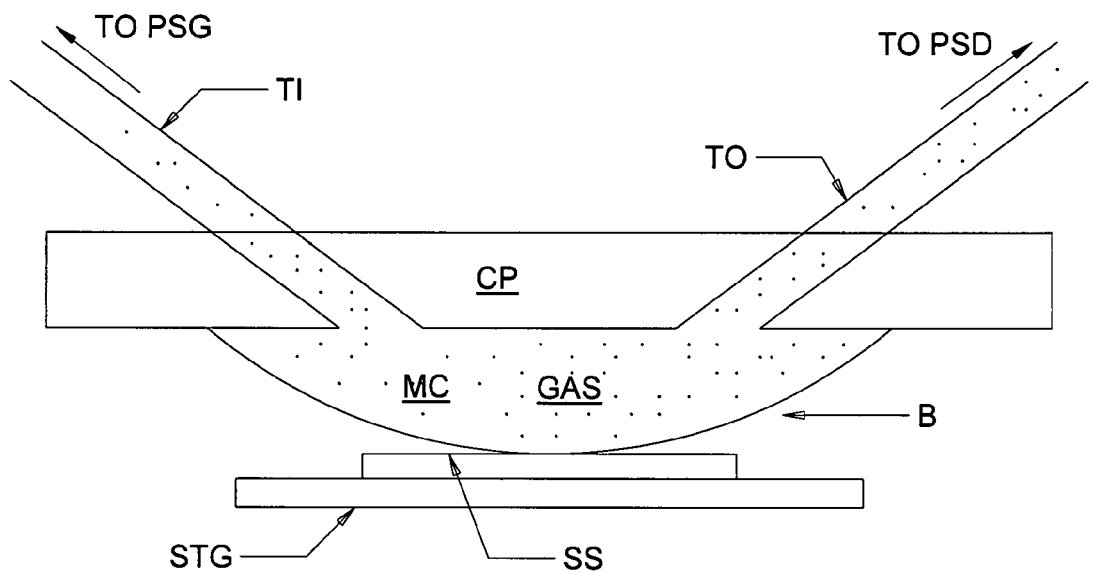

FIGS. 4a and 4b show a modified embodiment wherein a Bellows (B) is affixed to the Common Placement Means which in use is filled with gas such that it is placed directly adjacent to a surface of a Sample (SS). While the Common Placement Means (CP) can be moved to position the lower aspect of the Bellows (B) into contact with a Sample (SS), this embodiment enables contact via inflating the Bellows (B).

FIGS. 4c and 4d show two embodiments of a Bellows (B). FIG. 4c shows a small Hole (H) is present at a location whereat electromagnetic radiation would exit and impinge on a Sample (SS), and FIG. 4d shows that a region (T) which is transparent to applicable wavelengths is present. The remainder of the Bellows can be opaque to wavelengths in the UV, VUV, IR and NIR.

In general it should be appreciated that in FIGS. 3a, 3b, 3c, 4a, 4b, 5a and 5b that a "Mini-Chamber" (MC) is formed in which GAS is sequestered. In FIGS. 3a and 3c this is effected by vertically moving the Common Placement Means (CP) so that the Interface Means (I) is brought into contact therewith. In FIG. 3b said vertical motion provides contact between the Interface Means (I) and the Stage (STG). It is noted that the Common Placement Means (CP) can be of single or multiple element construction, and that contact can mean "substantial contact" where the Common Placement Means (CP) and the Interface Means (I) are nearly in contact with one another.

Figure 5A:
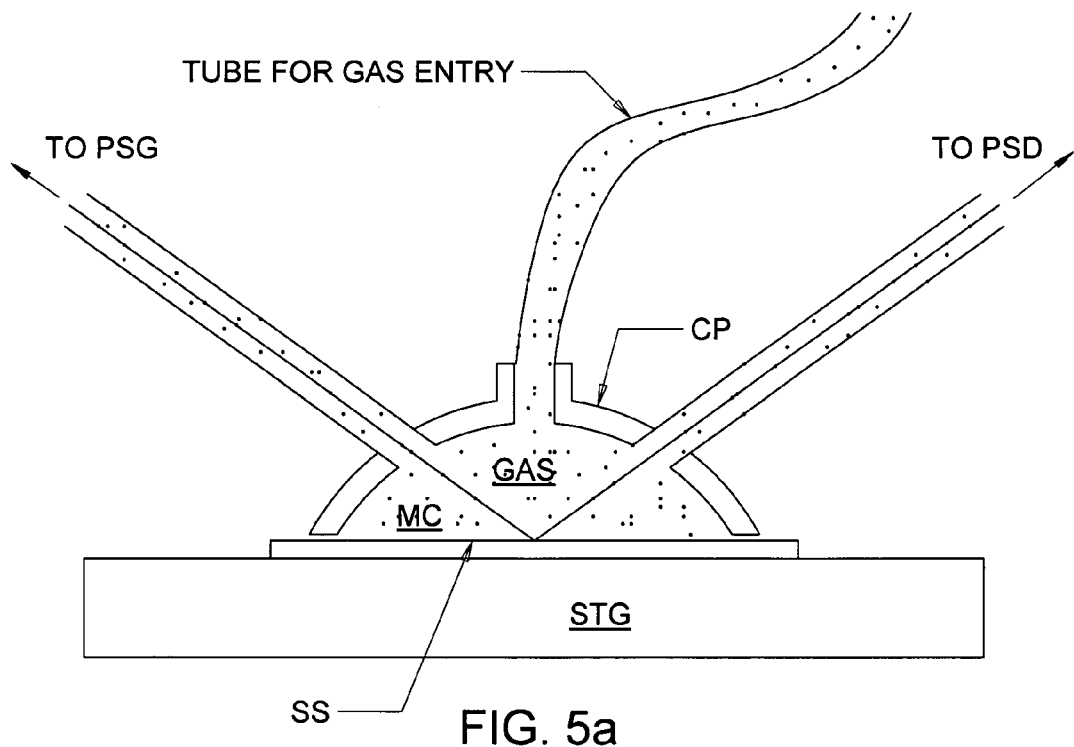
FIGS. 5a and 5b show embodiments of the present invention wherein a portion of a sample (SS) is sequestered in a mini-chamber.
Figure 5B:
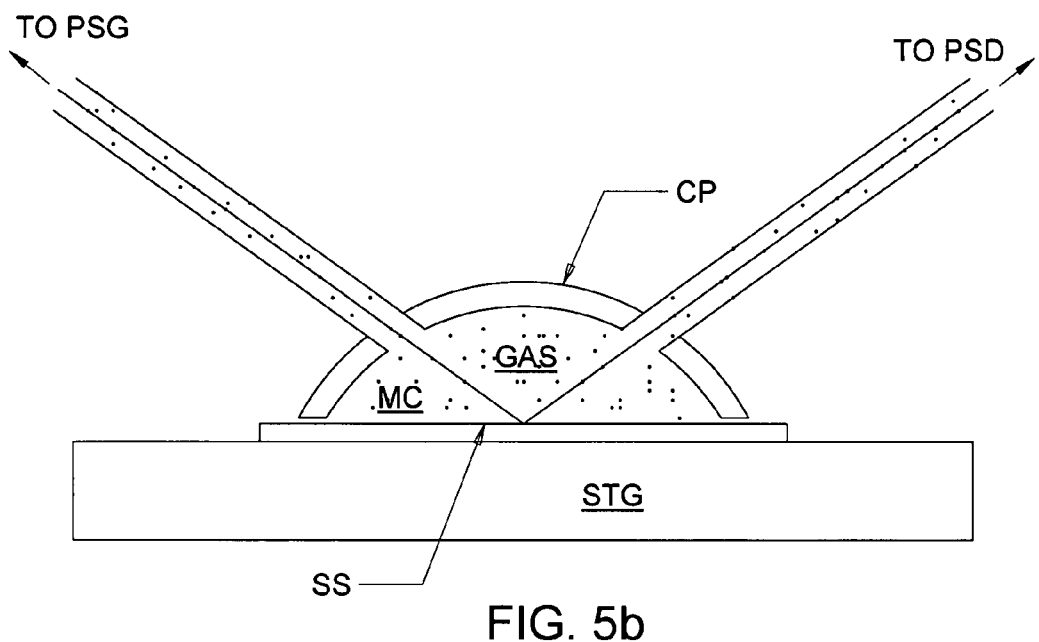

FIGS. 5a and 5b show embodiments of the present invention wherein a portion of a sample (SS) is sequestered in a Mini-Chamber (MC) which is formed by causing said Common Placement Means (CP) to actually contact a portion of a sample (SS). Note that the Common Placement Means (CP) need not have a planar surface facing the Sample (SS). The Common Placement Means (CP) can be constructed from one or more elements, and the Polarization State Generator (PSG) need not be affixed to the same element as is the Polarization State Detector (PSD) as long as said (PSG) and (PSD) can be caused to move together in a coordinated manner. The same is applicable to the embodiments shown in FIGS. 3a, 3b and 3c.

It is to be understood that while the foregoing presentation has focused on the use of gas to tangibly and concretely purge a "mini-chamber", it is possible to reverse to approach and apply an evacuation pump to tangibly and concretely decrease atmospheric content in a "mini-chamber", which can be, but is not necessarily followed by entering a purge gas thereinto.

It is also noted that while not limiting, the Stage (STG) for securing a Sample System can conveniently include a vacuum chuck which allows easily securing and releasing the sample by providing a suction, or not. In addition, the Stage (STG) for securing a Sample System can also contain a heating and/or cooling means for controlling the temperature of a sample.

In the forgoing, and in the Claims, recitation of "a beam having UV, VUV, IR and NIR wavelengths of electromagnetic radiation" is not to be interpreted to exclude the presence of Visible wavelengths. However, said Visible wavelengths are not specifically mentioned as they are not as susceptible to attenuation by $O_2$ and Water Vapor.

It is also noted that the Interface Means (I) can be rigid or non-rigid. Further, the Interface Means (I) can be in actual contact with, or in substantial contact with, (eg. a millimeter or more removed from actual contact with), a sample or stage and be considered slidably in contact therewith the criteria being that it is not so far removed so as to let gas flow therefrom unimpeded.

Figure 6:
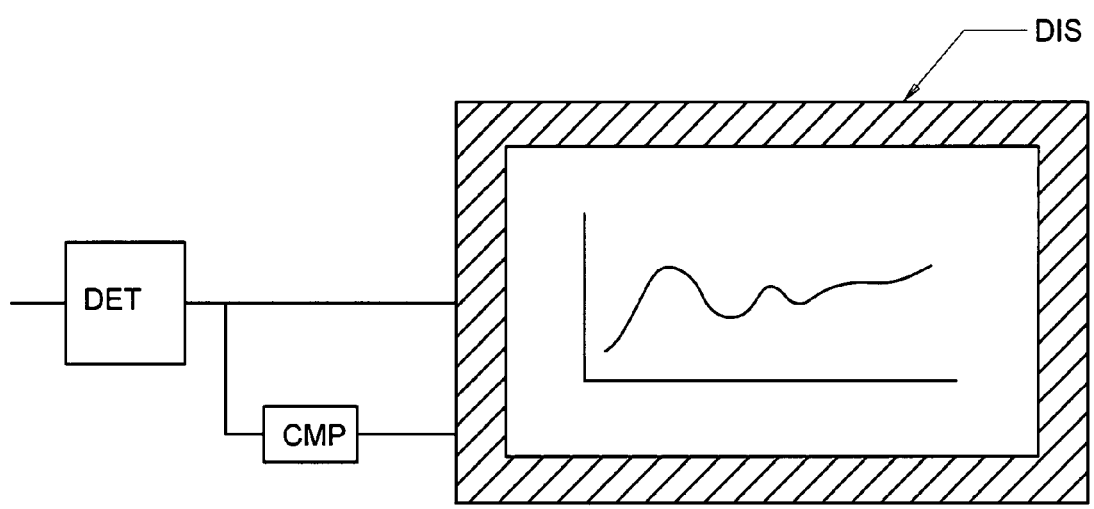
FIG. 6 is included to demonstrate that at least some data provided by the data detector (DET) and/or analyzed variations thereof can be displayed on a Display Means (DIS) or by other display means and/or at least some of the data obtained from said detector can be stored in machine readable media and/or cause at least some obtained data to be represented by a signal which is applied to provide a concrete and tangible result.

Finally, FIG. 6 demonstrates that data provided by the Data Detector (DET) and/or the results of analysis thereof by such as a Computer (CMP), can be displayed on a Display Means (DIS), or otherwise during practice of the methodology of the present invention. In general, FIG. 6 is included to indicate that at least some of the data from said detector and/or an analyzed version thereof can be stored in machine readable media and/or displayed electronically or by non-electronic means, and/or can be caused to be represented by a signal which is applied to provide a concrete and tangible result, such as control of a fabrication process.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for investigating a sample with electromagnetic radiation comprising:

a source of electromagnetic radiation and a detector of electromagnetic radiation oriented such that in use said source of electromagnetic radiation provides a beam of electromagnetic radiation at an angle of incidence to a surface of a sample, and said detector of electromagnetic radiation receives a resulting beam of electromagnetic radiation reflected therefrom;

said source and detector of electromagnetic radiation being functionally associated with a common placement means, and said sample being present on a separate stage;

said system further comprising means for causing relative motion between said source and detector of electromagnetic radiation as a unit, and said sample;

said system further comprising interface means that provides actual or substantial slidable contact with said separate stage such that a mini-chamber is formed thereby;

said system further comprising means for introducing gas into said mini-chamber;

such that in use said mini-chamber is caused to access, contain or make actual or substantial slidable contact with a portion of said sample or a support therefore.

2. An ellipsometer or polarimeter system for analyzing sample systems using electromagnetic radiation with wavelengths in the ultraviolet, vacuum ultraviolet, infrared or near infrared wavelength range, said ellipsometer system comprising a mini-chamber which encompasses at least a portion of a sample; said ellipsometer or polarimeter system further comprising:

a) source means for providing of a beam including ultraviolet, vacuum ultraviolet, infrared or near infrared wavelength range electromagnetic radiation;

b) polarization state setting means for setting a polarization state in at least a selected range of wavelengths in a beam including ultraviolet, vacuum ultraviolet, infrared or near infrared wavelength range electromagnetic radiation;

c) a means for placing and maintaining a sample system in a desired position and orientation, said means for placing and maintaining a sample system in a desired position and orientation being applied such that at least a portion of a sample surface can be accessed within said mini-chamber;

d) data detector means for receiving an electromagnetic beam which is caused to interact with a sample which is secured in place by said means for placing and maintaining a sample system in a desired position and orientation; and e) computer means for analyzing data provided by said data detector and/or storing at least some of the data and/or an analyzed version thereof in machine readable media and/or displaying at least some of the data and/or an analyzed version thereof electronically or by non-electronic means, and/or causing at least some obtained data and/or an analyzed version thereof to be represented by a signal which is applied to provide a concrete and tangible result;

said source means and polarization state setting means and data detector means all being functionally associated with a common placement means which can be positioned to actually or substantially slidably contact said means for placing and maintaining a sample system in a desired position and orientation via interface means, such that when said actual or substantial slidable contact is effected a mini-chamber is formed between said common placement means and said means for placing and maintaining a sample system in a desired position and orientation, said mini-chamber accessing at least a part of said sample surface;

said mini-chamber further having means functionally affixed thereto for effecting evacuation and/or entering purging gas into said mini-chamber;

such that in use a sample is caused to be positioned and oriented by said means for placing and maintaining a sample in a desired position and orientation, and actual or substantial slidable contact is realized between said common placement means and said means for placing and maintaining a sample in a desired position and orientation via said interface means, and purging gas is caused to be entered into said mini-chamber; and said source means for providing of a beam including ultraviolet, vacuum ultraviolet, infrared or near infrared wavelength range electromagnetic radiation is caused to provide a beam including ultraviolet vacuum ultraviolet, infrared and/or near infrared wavelengths, and said polarization state setting means for setting a polarization state in a selected range of wavelengths in a beam including electromagnetic radiation is caused to impose a polarization state thereupon and said beam of electromagnetic radiation is caused to reflect from said sample and enter said data detector;

and said computer means is applied to analyze data provided by said data detector and/or store at least some of the data and/or an analyzed version thereof in machine readable media and/or display at least some of the data and/or an analyzed version thereof electronically or by non-electronic means, and/or cause at least some obtained data and/or an analyzed version thereof to be represented by a signal which is applied to provide a concrete and tangible result.

3. An ellipsometer or polarimeter comprising sequentially a polarization state generator, a stage for supporting a sample and a polarization state detector, said ellipsometer or polarimeter further comprising a computer means;

said polarization state generator and polarization state detector being functionally associated with a common placement means which can be positioned to actually or substantially slidably contact said stage via interface means, such that when actual or substantial slidable contact is effected a mini-chamber is formed between said common placement means and said stage with said mini-chamber accessing at least a part of a surface of said sample;

said mini-chamber further having means functionally affixed thereto means for effecting evacuation and/or entering purging gas into said mini-chamber;

such that in use a sample is caused to be positioned on said stage and actual or substantial slidable contact is realized between said common placement means and said stage via said interface means, and purging gas is caused to be entered into said mini-chamber; and said polarization state generator is caused to provide a beam electromagnetic radiation which is directed to reflect from said sample and enter said data detector; and said computer means is applied to analyze data provided by said data detector and/or store at least some of the data and/or an analyzed version thereof in machine readable media and/or display at least some of the data and/or an analyzed version thereof electronically or by non-electronic means, and/or cause at least some obtained data and/or an analyzed version thereof to be represented by a signal which is applied to provide a concrete and tangible result.

4. A method of investigating a sample with spectroscopic electromagnetic radiation comprised of wavelengths which are absorbed by oxygen and/or water vapor, comprising the steps of:

in any functional order practicing steps a, a' and a":

a) providing a system for forming a mini-chamber which encloses a substantially enclosed space which accesses at least a portion of a sample, to which mini-chamber is functionally affixed a means for evacuating or purging said substantially enclosed space of oxygen and/or water vapor, and means for entering a beam of electromagnetic radiation thereinto, and a means for exiting electromagnetic radiation therefrom; and a') providing a source of a spectroscopic beam electromagnetic radiation comprised of wavelengths which are absorbed by oxygen and/or water vapor and wavelengths which are not absorbed by oxygen and/or water vapor; and a") providing a data detector of spectroscopic electromagnetic radiation and means for displaying detected data;

and then proceeding to practice steps b and c:

b) positioning a sample in said system for forming a mini-chamber which encloses a substantially enclosed space which accesses at least a portion of a sample;

c) causing said means for evacuating or purging said substantially enclosed space of oxygen and/or water vapor to tangibly and concretely evacuate or purge said substantially enclosed space of oxygen and/or water vapor, and causing said source of a spectroscopic beam electromagnetic radiation comprised of wavelengths which are absorbed by oxygen and/or water vapor to provide a beam of said electromagnetic radiation comprised of wavelengths which are absorbed by oxygen and/or water vapor to enter said means for entering a beam of electromagnetic radiation along a locus, such that it interacts with said sample, reflects therefrom, and exits said means for exiting electromagnetic radiation and enters said detector of spectroscopic electromagnetic radiation;

such that when said substantially enclosed space is sufficiently evacuated or purged of oxygen and/or water vapor, data is provided by said data detector for wavelengths which are absorbed by oxygen and/or water vapor; and d) performing at least one selection from the group consisting of:

storing at least some data provided by said data detector in machine readable media;

analyzing at least some of the data provided by said data detector and storing at least some of the results of said analysis in machine readable media;

displaying at least some data provided by said data detector by electronic and/or non-electronic means;

analyzing at least some of the data provided by said data detector and displaying at least some of the results of said analysis by electronic and/or non-electronic means;

causing at least some data provided by said data detector to produce a signal which is applied to provide a concrete and tangible result;

analyzing at least some of the data provided by said data detector and causing at least some thereof to produce a signal which is applied to provide a concrete and tangible result.

5. A method of investigating a sample with spectroscopic electromagnetic radiation comprised of wavelengths which are absorbed by oxygen and/or water vapor and wavelengths which are not absorbed by oxygen and/or water vapor, comprising the steps of:

in any functional order practicing steps a, a' and a":

a) providing a system for forming a mini-chamber which encloses a substantially enclosed space which accesses at least a portion of a sample, to which mini-chamber is functionally affixed a means for evacuating and/or purging said substantially enclosed space of oxygen and/or water vapor, and means for entering a beam of electromagnetic radiation thereinto, and a means for exiting electromagnetic radiation therefrom; and a') providing a source of a spectroscopic beam electromagnetic radiation comprised of wavelengths which are absorbed by oxygen and/or water vapor and wavelengths which are not absorbed by oxygen and/or water vapor; and a") providing a data detector of spectroscopic electromagnetic radiation and then proceeding to practice steps b and c:

b) positioning a sample in said system for forming a mini-chamber which encloses a substantially enclosed space which accesses at least a portion of a sample;

c) while causing said means for evacuating or purging said substantially enclosed space of oxygen and/or water vapor to tangibly and concretely evacuate or purge said substantially enclosed space of oxygen and/or water vapor, causing said source of a spectroscopic beam electromagnetic radiation comprised of wavelengths which are absorbed by oxygen and/or water vapor and wavelengths which are not absorbed by oxygen and/or water vapor, to provide a beam of said electromagnetic radiation comprised of wavelengths which are absorbed by oxygen and/or water vapor and wavelengths which are not absorbed by oxygen and/or water vapor and cause it to enter said means for entering a beam of electromagnetic radiation along a locus, such that it interacts with said sample and exits said means for exiting electromagnetic radiation and enters said detector of spectroscopic electromagnetic radiation;

such that during the evacuation or purging process, while oxygen and/or water vapor is still present in said substantially enclosed space in sufficient quantity to absorb said wavelengths which are absorbed by said oxygen and/or water vapor, data is provided by said data detector for wavelengths which are not absorbed by oxygen and/or water vapor, and such that once said substantially enclosed space is sufficiently evacuated or purged of oxygen and/or water vapor, data is provided by said data detector for wavelengths which are absorbed by oxygen and/or water vapor and d) performing at least one selection from the group consisting of:

storing at least some data provided by said data detector in machine readable media;

analyzing at least some of the data provided by said data detector and storing at least some of the results of said analysis in machine readable media;

displaying at least some data provided by said data detector by electronic and/or non-electronic means;

analyzing at least some of the data provided by said data detector and displaying at least some of the results of said analysis by electronic and/or non-electronic means;

causing at least some data provided by said data detector to produce a signal which is applied to provide a concrete and tangible result;

analyzing at least some of the data provided by said data detector and causing at least some thereof to produce a signal which is applied to provide a concrete and tangible result.

* * * * *